United States Patent [19]

Higo et al.

[11] Patent Number: 5,733,900
[45] Date of Patent: Mar. 31, 1998

[54] PERCUTANEOUS ADMINISTRATION BASE COMPOSITION AND PERCUTANEOUS ADMINISTRATION MEDICINAL COMPOSITION COMPRISING SAID BASE COMPOSITION AND MEDICINE

[75] Inventors: Naruhito Higo; Ken-ichi Komori, both of Tsukuba, Japan

[73] Assignee: Hisamitsu Pharmaceutical Co., Inc., Tosu, Japan

[21] Appl. No.: 702,449
[22] PCT Filed: Apr. 19, 1995
[86] PCT No.: PCT/JP95/00774
§ 371 Date: Sep. 26, 1996
§ 102(e) Date: Sep. 26, 1996
[87] PCT Pub. No.: WO95/28914
PCT Pub. Date: Nov. 2, 1995

[30] Foreign Application Priority Data

Apr. 21, 1994 [JP] Japan ................ 6-107584

[51] Int. Cl.$^6$ .......... A61K 31/045; A61K 31/19; A61K 31/22; A61K 31/34
[52] U.S. Cl. .......... 514/171; 514/315; 514/473; 514/549; 514/557; 514/724; 514/738; 514/552
[58] Field of Search ................ 514/171, 315, 514/473, 549, 552, 557, 722, 724, 738

[56] References Cited

FOREIGN PATENT DOCUMENTS 9402119 2/1994 WIPO.

*Primary Examiner*—Phyllis G. Spivack
*Attorney, Agent, or Firm*—Kubovcik & Kubovcik

[57] ABSTRACT

A percutaneous administration base composition is disclosed comprising an absorption promoter, a moisture-retaining agent, water, an irritation-lessening agent, a lower alcohol and an organic acid wherein a medicine is optionally contained in the base composition.

14 Claims, No Drawings

PERCUTANEOUS ADMINISTRATION BASE COMPOSITION AND PERCUTANEOUS ADMINISTRATION MEDICINAL COMPOSITION COMPRISING SAID BASE COMPOSITION AND MEDICINE

TECHNICAL FIELD

This invention relates to a percutaneous administration base composition (or percutaneously administrable base composition) which enhances a medicine in percutaneous absorbability and is a low irritative to the skin and also relates to a percutaneous administration medicinal composition in which a medicine is contained in said base composition.

BACKGROUND ART

Methods of administering a medicine (or drug) which have heretofore been known, include those of peroral, rectal, hypodermic and intravenous administrations, among which peroral administration has widely been adopted. However, peroral administration of a medicine is disadvantageous in that, for example, the medicine is subject to primary metabolism at the liver after the absorption thereof, and an unduly high concentration of the medicine is temporarily appreciated after the administration thereof. Further, it has often been reported that side effects such as gastroenteric tract troubles, nausea and lack of appetite are caused when a medicine is perorally administered.

Percutaneous administration of a medicine has recently been noted in attempts to avoid such disadvantages of peroral administration and to meet the requirements of safe and sustained absorption of the medicine. In view of the above, the development of medicines for external application has been positively promoted and the medicines so developed have already been on the market.

Such percutaneous administration preparations, however, are yet often insufficient in percutaneous absorption of the medicine and, therefore, it cannot be said in fact that the object to provide a desired preparation is fully attained. More particularly, since the normal skin originally has a barrier function to prevent foreign matters from permeating into the body, the base singly used as such in an ordinary percutaneous administration preparation will not let the medicine used therein be fully percutaneously absorbed. It is thus required that the permeability of the medicine through the homey layer of the skin be controlled to enhance the medicine in percutaneous absorbability.

To this end, it is generally tried that a so-called percutaneous absorption promoter is added to the base. The absorption promoters which have already been proposed, include a combination of dimethylacetoamide with ethyl alcohol, isopropyl alcohol, isopropyl palmitate or the like (U.S. Pat. No. 3,472,931); a combination of 2-pyrrolidone with a suitable oil or with an ester of a straight-chain fatty acid and an alcohol (U.S. Pat. No. 4,017,641); and a combination of a lower alcohol with one of an alcohol having 7–20 carbon atoms, an aliphatic hydrocarbon having 5–30 carbon atoms, an ester of an aliphatic carboxylic acid with an alcohol, a mono- or diether having 10–24 carbon atoms and a ketone having 11–15 carbon atoms, and also with water (Japanese Pat. Appln. Laid-Open Gazette No. Sho 61-249934).

It cannot be said yet, however, that the above conventional absorption promoters and absorption promoting compositions are sufficiently safe for the skin. Further, it is attempted to enhance a basic medicine in percutaneous permeability by having an organic acid contained in a preparation comprising the basic medicine and, however, such attempt does not exert sufficient remedial effects as yet. Furthermore, a low irritative absorption promoting composition is reported in Japanese Pat. Appln. Laid-Open Gazette No. Hei 2-115131; however, this composition is still appreciated to be irritative to the skin site where it is administered in case of subjects who are highly susceptible to an alcohol.

DISCLOSURE OF THE INVENTION

This invention has been made to solve the problems of the above-mentioned conventional techniques and has for its object to provide a percutaneous administration base composition which enhances a medicine in percutaneous absorbability when the medicine is contained in the base composition and is remarkably low in irritation to the skin where a medicinal composition is administered and also to provide an excellently safe percutaneous administration medicinal composition comprising said base composition and a medicine.

This invention resides in not only a percutaneous administration base composition comprising an absorption promoter (sorbefacient), moisture-retaining agent (humectant), water, irritation-lessening agent, lower alcohol and organic acid thereby to solve the above problems, but also a percutaneous administration medicinal composition wherein a medicine is contained in said base composition.

The percutaneous administration base composition of this invention will enhance a medicine in percutaneous permeability when the medicine is contained therein, is less in skin irritability and excels in physical stability of the base composition. In addition, the percutaneous administration medicinal composition of this invention enables the medicine contained therein to be excellent in percutaneous permeability, physical stability, low irritability to the skin, and the like.

This invention will be explained below in more detail.

The absorption promoters usable in this invention are preferably medium or long chain fatty acids, aliphatic alcohols or fatty acid esters, with those having 7–20 carbon atoms being particularly preferred. It has been found that particularly lauryl alcohol and myristyl alcohol exhibit high absorption promotability or accelerability of the medicine and are comparatively less irritative to the skin.

The moisture-retaining agents used in this invention preferably include aliphatic polyhydric alcohols and sugar alcohols. These alcohols include sorbitol, polyethylene glycol, diglycerin, propylene glycol, butylene glycol, dipropylene glycol, sodium pyrrolidone carboxylate, ethyl carbitol, D-xylytol, glycerin and hyaluronic acid, among which glycerin and polyethylene glycol are particularly preferred.

The water component used in this invention may be purified water or a buffer, and it is desired that the water and buffer be adjusted to a pH of 5–7. In addition, the buffer may be any one only if it has a pH of 5–7 which is applicable to human bodies, and is exemplified by a maleic acid buffer, a maleic acid-Tris buffer, an acetic acid-sodium acetate buffer, a Tris buffer, a phosphoric acid buffer, a phosphoric acid-citric acid buffer, an imidazole buffer, a S-collidine buffer, a triethanolamine buffer or a pyrophosphoric acid buffer, with the phosphoric acid-citric acid buffer and the phosphoric acid buffer being particularly preferred. Further, the buffers usable in this invention are not limited to the above-mentioned ones, and they may be any one having a pH value of 5–7 which is applicable to human bodies and can be obtained by combining an acid with a base.

The preferable irritation-lessening agents used in this invention include medium or long chain fatty acid esters, sorbitol-fatty acid esters and mixtures thereof with glycerin monooleate, glycerin monolaurate, sorbitan-monolaurate and mixtures thereof being particularly preferred as exhibiting remarkable dermal irritation-lessening effects.

The particularly preferable lower alcohols used in this invention are ethanol and isopropanol.

The organic acids used in this invention include acetic acid, lactic acid, N-2-hydroxyethylpiperidine-N'-2-ethanesulfonic acid which is hereinafter abbreviated as HEPES, dehydrocholic acid and the salts thereof. In addition, the organic acids usable herein also include water-soluble inorganic salts of organic acids with sodium acetate, sodium dehydrocholate and sodium lactate being particularly noted. According to this invention, the presence of the organic acid in the optimum concentration will enable the amount of a medicine permeated through the skin to be remarkably increased without strengthening dermal irritation due to the medicine. This tendency will be particularly noted when the organic acid is contained in a suitable proportion.

The percutaneous administration base composition of this invention preferably comprises, by weight, 0.1–10% of an absorption-promoting agent, 15–40% of a moisture-retaining agent, 20–70% of water, 0.5–10% of an irritation-lessening agent, 10–40% of a lower alcohol and 0.1–10% of an organic acid, all the percentages for said components totalling 100%.

In cases where the contents of the components comprised in such a base cmposition as above are in ranges respectively outside of said ones according to this invention, a medicine contained in said composition and said composition itself will exhibit the following disadvantages when applied to the skin.

If the content of the absorption promoter is less than 0.1% by weight in a base composition, a medicine contained therein will not be appreciated to exert its percutaneous permeability; further, the content thereof exceeding 10% by weight in the composition will be appreciated to cause the composition to bring about skin irritation. If the content of the moisture-retaining agent is less than 15% by weight in the composition, the composition will cause skin irritation; on the other hand, if the content thereof exceeds 40% by weight, the medicine contained in the composition will be liable to be remarkably lessened in percutaneous permeability. If the content of water is less than 20% by weight, the composition will cause skin irritation; on the other hand, if the content thereof exceeds 70% by weight, the medicine will be liable to be remarkably worsened in percutaneous permeability. If the content of the irritation-lessening agent is less than 0.5% by weight, none of irritation-lessening effects of the composition will be appreciated; further, the content thereof exceeding 10% by weight is not desirable since the composition will contrarily exhibit skin irritation. If the content of the lower alcohol is less than 10% by weight, the medicine contained in the composition will be remarkably lowered in percutaneous permeability; on the other hand, the content thereof exceeding 40% by weight is not preferable since the composition will be liable to increase skin irritation. If the content of the organic acid is less than 0.1% by weight in the composition, the medicine contained therein will be remarkably lessened in percutaneous permeability; in addition,. the content thereof exceeding 10% by weight will remarkably lessen the medicine in percutaneous premeability similarly to the above-mentioned case and, furthermore, the composition will cause undesirable skin irritation.

The percutaneous administration base composition of this invention appropriately contains each base component in such an amount as will be specified hereinbelow. Namely, the content of the absorption promoter ranges preferably from 0.1 to 10% by weight, more preferably from 0.3 to 8% by weight and most preferably from 0.5 to 3% by weight. The content of the moisture-retaining agent ranges preferably from 15 to 40% by weight, more preferably from 20 to 38% by weight and most perferably from 25 to 35% by weight. The content of water ranges preferably from 20 to 70% by weight, more preferably from 25 to 60% by weight and most preferably from 30 to 50% by weight. The content of the irritation-lessening agent ranges preferably from 0.5 to 10% by weight, more preferably from 1 to 7% by weight and most preferably from 1 to 5% by weight. The content of the lower alcohol ranges preferably from 10 to 40% by weight, more preferably from 15 to 30% by weight and most preferably from 20 to 25% by weight. The content of the organic acid described above ranges preferably from 0.1 to 10% by weight, more preferably from 0.3 to 8% by weight and most preferably from 0.5 to 5% by weight. As previously mentioned, all the percentages for the base components of the base composition total 100%. A particularly excellent percutaneous administration base composition can be obtained by selecting the contents of these base components so that the contents selected constitute a more preferable or the most preferable weight ratio among them.

The medicines which may be contained in the percutaneous administration base composition of this invention are not particularly restricted so long as they are percutaneously absorbable. They include hypnotic/sedatives (nitrazepam, barbital, etc.), antipyretic, anti-inflammatory, analgesic agents (ketoprofen, indomethacin, butorphanol tartrate, pentazocine, loxoprofen, diclofenac, felbinac, etc.), stimulant/analeptic agents (methamphetamine, bemegride, etc.), psychoneurotic agents (meprobamate, imipramine, etc.), local anesthetics (lidocaine, procaine, etc.), drugs for hyperuricemia (allopurinol, benzbromarone, etc.), drugs for urination disorders (oxybutynin, etc.), skeletal muscle relaxants (tizanidine hydrochloride, eperisone hydrochloride, dantrolene, etc.), autonomic drugs (carpronium, neostigmine, etc.), antiparkinson agents, antihistaminic agents (mequitazine, diphenhydramine, etc.), bronchodilating agents (tulobuterol hydrochloride, sodium cromoglycate), cardiotonic agents (digoxin, aminophylline, etc.), vasodilator agents (nitroglycerin, isosorbide nitrate, nifedipine, etc.), peripheral vasodilator agents (nicametate, cyclandelate, etc.), drugs for circulatory organs (flunarizine, ibudilast, etc.), drugs for arrhythmia (atenolol, alprenolol hydrochloride, etc.), antiallergic agents (tranilast, ketotifen fumarate, mequitazine, etc.), antivertigo agents (betahistine, diphenidol, etc.), narcotic analgesics (morphine, fentanyl citrate, etc.), cortex hormone agents (prednisolone, betamethasone, etc.), male hormone agents (testosterone, etc.), follicle corpus luteal hormone agents (estradiol, estriol, etc.), dermatological sterilization agents, wound protectors, external preparations for purulent diseases (kanamycin, etc.) and drugs for parasitic skin diseases (miconazole, etc.). Use may be made of either one of these medicines or a combination of two or more thereof. Needless to say, medicines in the form of publicly known inorganic or organic salts are also included in those containable in the composition of this invention. The above-mentioned medicines may each usually be contained in the percutaneous administration medicinal composition in an amount of from 0.001 to 20% by weight thereof.

The percutaneous administration medicinal composition of this invention may be administered in the form of gels, creams, liniments, reserver-type patches, cataplasmas, etc. If needed, a gelling agent (thickener) may be added to the composition. The appropriate gelling agents include carboxyvinyl polymers, polysodium acrylate, polyvinylpyrrolidone, hydroxypropylmethylcellulose, hydroxyethylcellulose, hydroxypropylcellulose, methylcellulose, carboxymethylcellulose and salts thereof.

If necessary, there may be added to the composition additives such as ultraviolet absorbers, antioxidants and preservatives. The appropriate ultraviolet absorbers include publicly known p-aminobenzoic acid derivatives, anthranilic acid derivatives, salicylic acid derivatives, coumalic acid derivatives, amino acid derivatives, benzotriazole derivatives, tetrazole derivatives, imidazoline derivatives, pyrimidine derivatives, dioxane derivatives, furan derivatives, pyrone derivatives, camphor derivatives, nucleic acid derivatives, allantoin derivatives, nicotinic acid derivatives, shikonin and vitamin 6 derivatives. In particular, benzophenone derivatives such as 2-hydroxy-4-methoxybenzophenone derivatives can be appropriately used as the ultaviolet absorbers.

The antioxidants include ascorbic acid, stearic acid esters, sodium ascorbate, tocopherol (d-, l- and dl-isomers of α-tocopherol, β-tocopherol, γ-tocopherol, δ-tocopherol, etc.) and ester derivatives thereof, nordihydroguaiaretic acid, dibutylhydroxytoluene, butylhydroxyanisole, tert-butylhydroxynongallic acid esters (ethyl ester, propyl ester, isoamyl ester, etc.) and 1-oxo-3-methyl-4-isopropylbenzene.

The preservatives include benzoic acid, sodium benzoate, ethyl p-hydroxybenzoate, propyl p-hydroxybenzoate and butyl p-hydroxybenzoate.

BEST MODE FOR CARRYING OUT THE INVENTION

To further illustrate this invention in greater detail, the following Examples will be given. In these Examples and Comparative Examples, all percentages are by weight and the content (% by weight) of a medicine means a ratio thereof to the whole percutaneous administration medicinal composition.

EXAMPLE 1

| | |
|---|---|
| Ethanol | 24% |
| purified water | 42.5% |
| glycerol | 25% |
| lauryl alcohol | 0.5% |
| glycerol monooleate | 3% |
| sorbitan monolaurate | 1% |
| sodium acetate | 0.5% |
| carboxymethylcellulose sodium | 3.5% |
| total | 100%. |

To a mixture of the above components was added 3% of tulobuterol hydrochloride thereby to give a percutaneous administration medicinal composition.

EXAMPLE 2

| | |
|---|---|
| Ethanol | 24% |
| buffer (pH 6.8, phosphoric acid-citric acid buffer) | 34% |
| polyethylene glycol 300 | 25% |
| lauryl alcohol | 3% |
| sorbitan monolaurate | 2% |
| glycerol monooleate | 8% |
| sodium acetate | 2% |
| hydroxypropylmethylcellulose 4000 | 2% |
| total | 100%. |

To a mixture of the above components was added 2% of fentanyl titrate thereby to give a percutaneous administration medicinal composition.

EXAMPLE 3

| | |
|---|---|
| Ethanol | 24% |
| purified water | 24% |
| polyethylene glycol 400 | 25% |
| lauryl alcohol | 10% |
| glycerol monolaurate | 8% |
| sorbitan monolaurate | 2% |
| sodium lactate | 5% |
| hydroxypropylmethylcellulose 4000 | 2% |
| total | 100%. |

To a mixture of the above components was added 5% of alprenolol hydrochloride thereby to give a percutaneous administration medicinal composition.

EXAMPLE 4

| | |
|---|---|
| Ethanol | 15% |
| buffer (pH 6.8, phosphoric acid buffer) | 28% |
| polyethylene glycol 300 | 30% |
| myristyl alcohol | 5% |
| glycerol monooleate | 5% |
| HEPES | 15% |
| hydroxypropylmethylcellulose 4000 | 2% |
| total | 100%. |

To a mixture of the above components was added 5% of ibudilast thereby to give a percutaneous administration medicinal composition.

EXAMPLE 5

| | |
|---|---|
| Ethanol | 24% |
| purified water | 44% |
| polyethylene glycol 300 | 25% |
| myristyl alcohol | 2% |
| sorbitan monolaurate | 2% |
| acetic acid | 1% |
| hydroxypropylmethylcellulose 4000 | 2% |
| total | 100%. |

To a mixture of the above components was added 5% of atenolol thereby to give a percutaneous administration medicinal composition.

EXAMPLE 6

| | |
|---|---|
| Isopropanol | 20% |
| purified water | 39% |
| polyethylene glycol 400 | 35% |

-continued

| | |
|---|---|
| myristyl alcohol | 1% |
| sorbitan monolaurate | 1% |
| acetic acid | 0.5% |
| sodium acetate | 1% |
| hydroxypropylmethylcellulose 4000 | 2.5% |
| total | 100%. |

To a mixture of the above components was added 3% of oxybutynin hydrochloride thereby to give a percutaneous administration medicinal composition.

EXAMPLE 7

| | |
|---|---|
| Ethanol | 24% |
| buffer (pH5, acetic acid buffer) | 44% |
| polyethylene glycol 300 | 25% |
| lauryl alcohol | 0.50% |
| glycerol monooleate | 3% |
| sorbitan monolaurate | 1% |
| sodium acetate | 0.5% |
| hydroypropylmethylcellulose 4000 | 2% |
| total | 100%. |

To a mixture of the above components was added 3% of tizanidine hydrochloride thereby to give a percutaneous administration medicinal composition.

COMPARATIVE EXAMPLE 1 (containing no organic acid)

| | |
|---|---|
| Ethanol | 24% |
| buffer (pH7, phosphoric acid buffer) | 43% |
| glycerol | 25% |
| lauryl alcohol | 0% |
| glycerol monooleate | 3% |
| sorbitan monolaurate | 1% |
| carboxymethylcellulose sodium | 3.5% |
| total | 100%. |

To a mixture of the above components was added 3% of tulobuterol hydrochloride thereby to give a percutaneous administration medicinal composition.

COMPARATIVE EXAMPLE 2 (containing no organic acid)

| | |
|---|---|
| Isopropanol | 20% |
| buffer (pH6, citric acid buffer) | 26% |
| polyethylene glycol 400 | 35% |
| myristyl alcohol | 15% |
| sorbitan monolaurate | 2% |
| hydroxypropylmethylcellulose 4000 | 2% |
| total | 100%. |

To a mixture of the above components was added 3% of oxybutynin hydrochloride thereby to give a percutaneous administration medicinal composition.

COMPARATIVE EXAMPLE 3 (according as Japanese Patent Application Laid-Open Gazette No. Sho 61-249934) (containing no organic acid)

| | |
|---|---|
| Ethanol | 49% |
| purified water | 47% |
| lauryl alcohol | 1% |
| carboxymethylcellulose sodium | 3% |
| total | 100%. |

To a mixture of the above components was added 5% of fentanyl citrate thereby to give a percutaneous administration medicinal composition.

COMPARATIVE EXAMPLE 4 (containing no organic acid)

| | |
|---|---|
| Ethanol | 20% |
| purified water | 37% |
| polyethylene glycol 400 | 25% |
| sorbitan monolaurate | 15% |
| carboxymethylcellulose sodium | 3% |
| total | 100%. |

To a mixture of the above components was added 5% of alprenolol hydrochloride thereby to give a percutaneous administration medicinal composition.

COMPARATIVE EXAMPLE 5 (containing no irritation-lessening agent)

| | |
|---|---|
| Ethanol | 20% |
| purified water | 37% |
| myristyl alcohol | 5% |
| glycerol | 15% |
| acetic acid | 20% |
| carboxymethylcellulose sodium | 3% |
| total | 100%. |

To a mixture of the above components was added 3% of tulobuterol hydrochloride thereby to give a percutaneous administration medicinal composition.

COMPARATIVE EXAMPLE 6 (containing neither absorption promoter nor irritation-lessening agent)

| | |
|---|---|
| Ethanol | 30% |
| buffer (pH7, phosphoric acid buffer) | 59% |
| citric acid | 11% |
| total | 100%. |

To a mixture of the above components was added 5% of atenolol thereby to give a percutaneous administration medicinal composition.

TEST EXAMPLE

The percutaneous administration medicinal compositions obtained in the above Examples 1 to 7 and Comparative Examples 1 to 6, were each tested for percutaneous permeation of the medicine in vitro with the use of extirpated hairless mouse skin. Also, the percutaneous administration medicinal compositions were subjected to a skin irritation test. This test was carried out as follows. The compositions were each applied to the skin of each of human subjects. The compositions so applied were peeled from the skin of the subjects 24 hours after their application to the skin. A skin irritation test was made for evaluation scores on each subject at the skin spot (from which the applied composition was peeled) two times, that is, just soon and 24 hours after the peeling of the applied composition in order to find two evaluation scores which are determined from Table 2. The higher one of the two scores so found was taken as the irritation value for a particular subject, and the higher scores for the individual subjects were summed up and then the sum was divided by number of the subjects thereby to obtain a skin irritation value (SI value). Table 1 summarizes the results.

$$SI\ value = \frac{\text{sum of higher one of two scores obtained for individual subjects immediately after peeling of applied composition and 24 hours after peeling thereof}}{\text{number of subjects}} \times 100$$

TABLE 1

| Ex. & Comp. Ex. | Amount of Medicine permeating through Skin (μg/cm²/hr) | Skin Irritation value (SI value) |
|---|---|---|
| Ex. 1 | 180.8 | 11.0 |
| Ex. 2 | 210.7 | 13.0 |
| Ex. 3 | 320.5 | 22.0 |
| Ex. 4 | 377.5 | 20.0 |
| Ex. 5 | 30.5 | 8.0 |
| Ex. 6 | 112.2 | 16.0 |
| Ex. 7 | 50.7 | 3.0 |
| Comp. Ex. 1 | 50.2 | 11.0 |
| Comp. Ex. 2 | 90.0 | 14.0 |
| Comp. Ex. 3 | 300.1 | 190.0 |
| Comp. Ex. 4 | 90.2 | 20.0 |
| Comp. Ex. 5 | 170.7 | 80.0 |
| Comp. Ex. 6 | 11.5 | 20.0 |

TABLE 2

| Evaluation | Conditions | Score |
|---|---|---|
| − | no response | 0 |
| ± | slight erythema | 0.5 |
| + | erythema (rubefaction) | 1.0 |
| ++ | erythema + edema (overall rising) | 2.0 |
| +++ | erythema + edema + papule or small bulla | 3.0 |

INDUSTRIAL APPLICABILITY

In the percutaneous administration medicinal composition of this invention comprising the components as described above, the medicine contained therein can be efficiently and continuously absorbed percutaneously directly into the circulating blood. Further, the composition of this invention is a remarkably low irritative to the skin where it is administered.

Furthermore, the percutaneous administration medicinal composition of this invention makes it possible to sustain the effective concentration of the medicine in the blood without the medicine being subjected to the primary metabolism in the liver due to the first pass effect as observed in case of peroral administration. It is furthermore expected that the percutaneous administration medicinal composition is free from any side effects which might be caused by a rapid increase in the concentration of the medicine in the blood as observed in peroral administration. Accordingly, the percutaneous administration medicinal composition of this invention is useful particularly as an external preparation to be administered percutaneously.

What is claimed is:

1. A percutaneous administration base composition comprising an absorption promoter, a moisture-retaining agent, water, an irritation-lessening agent, a lower alcohol, and an organic acid selected from the group consisting of acetic acid, lactic acid, N-2-hydroxyethylpiperidine-N'-2-ethanesulfonic acid, dehydrocholic acid and the salts thereof.

2. A percutaneous administration base composition according to claim 1, wherein the absorption promoter is lauryl alcohol or myristyl alcohol, the moisture-retaining agent is glycerin or polyethylene glycol, the water is purified water, the irritation-lessening agent is glycerin monooleate, glycerin monolaurate or sorbitan-monolaurate, and the lower alcohol is ethanol or isopropanol.

3. A percutaneous administration base composition according to claim 1 or 2, comprising, by weight, 0.1–10% of the absorption promoter, 15–40% of the moisture-retaining agent, 20–70% of the water, 0.5–10% of the irritation-lessening agent, 10–40% of the lower alcohol and 0.1–10% of the organic acid selected from the group consisting of acetic acid, lactic acid, N-2-hydroxyethylpiperidine-N'-2-ethanesulfonic acid, dehydrocholic acid and the salts thereof, all the percentages for said components totalling 100%.

4. A percutaneous administration base composition according to claim 3, comprising, by weight, 0.3–8% of the absorption promoter, 20–38% of the moisture-retaining agent, 25–60% of the water, 1–7% of the irritation-lessening agent, 15–30% of the lower alcohol and 0.3–8% of the organic acid selected from the group consisting of acetic acid, lactic acid, N-2-hydroxyethylpiperidine-N'-2-ethanesulfonic acid, dehydrocholic acid and the salts thereof.

5. A percutaneous administration base composition according to claim 4, comprising, by weight, 0.5–3% of the absorption promoter, 25–35% of the moisture-retaining agent, 30–50% of the water, 1–5% of the irritation-lessening agent, 20–25% of the lower alcohol and 0.5–5% of the organic acid selected from the group consisting of acetic acid, lactic acid, N-2-hydroxyethylpiperidine-N'-2-ethanesulfonic acid, dehydrocholic acid and the salts thereof.

6. A percutaneous administration base composition according to claim 1 or 2 wherein the water is purified water each having a pH of 5–7.

7. A percutaneous administration medicinal composition wherein a medicine is contained in the percutaneous administration base composition according to claim 1 or 2.

8. A percutaneous administration base composition comprising an absorption promoter, a moisture-retaining agent, a buffer, an irritation-lessening agent, a lower alcohol, and an organic acid selected from the group consisting of acetic acid, lactic acid, N-2-hydroxyethylpiperidine-N'-2-ethanesulfonic acid, dehydrocholic acid and the salts thereof.

9. A percutaneous administration base composition according to claim 8, wherein the absorption promoter is lauryl alcohol or myristyl alcohol, the moisture-retaining agent is glycerin or polyethylene glycol, the irritation-lessening agent is glycerin monooleate, glycerin monolaurate or sorbitan monolaurate, and the lower alcohol is ethanol or isopropanol.

10. A percutaneous administration base composition according to claim 8 or 9, comprising, by weight, 0.1–10% of the absorption promoter, 15–40% of the moisture-retaining agent, 20–70% of the buffer, 0.5–10% of the irritation-lessening agent, 10–40% of the lower alcohol and 0.1–10% of the organic acid selected from the group consisting of acetic acid, lactic acid, N-2-hydroxyethylpiperidine-N'-2-ethanesulfonic acid, dehydrocholic acid and the salts thereof, all the percentages for said components totaling 100%.

11. A percutaneous administration base composition according to claim 10, comprising, by weight, 0.3–8% of the absorption promoter, 20–38% of the moisture-retaining agent, 25–60% of the buffer, 1–7% of the irritation-lessening agent, 15–30% of the lower alcohol and 0.3–8% of the organic acid selected from the group consisting of acetic acid, lactic acid, N-2-hydroxyethylpiperidine-N'-2-ethanesulfonic acid, dehydrocholic acid and the salts thereof.

12. A percutaneous administration base composition according to claim 11, comprising, by weight, 0.5–3% of the absorption promoter, 25–35% of the moisture-retaining agent, 30–50% of the buffer, 1–5% of the irritation-lessening agent, 20–25% of the lower alcohol and 0.5–5% of the organic acid selected from the group consisting of acetic acid, lactic acid, N-2-hydroxyethylpiperidine-N'-2-ethanesulfonic acid, dehydrocholic acid and the salts thereof.

13. A percutaneous administration base composition according to claim 8 or 9 wherein the buffer has a pH of 5–7.

14. A percutaneous administration medicinal composition wherein a medicine is contained in the percutaneous administration base composition according to claim 8 or 9.

* * * * *